(12) United States Patent
Lemaitre et al.

(10) Patent No.: US 6,458,335 B1
(45) Date of Patent: Oct. 1, 2002

(54) PRODUCTION OF POWDERS

(75) Inventors: Jacques Lemaitre, La Conversion; Nathalie Jongen, Preverenges, both of (CH); Robert Vacassy, Evian (FR); Paul Bowen, Nyon (CH)

(73) Assignee: Calcitech Ltd., Hamilton (BM)

( * ) Notice: Subject to any disclaimer, the term of this patent is extended or adjusted under 35 U.S.C. 154(b) by 0 days.

(21) Appl. No.: 09/230,026

(22) PCT Filed: Jul. 15, 1997

(86) PCT No.: PCT/EP97/03817

§ 371 (c)(1),
(2), (4) Date: Sep. 7, 1999

(87) PCT Pub. No.: WO98/02237

PCT Pub. Date: Jan. 22, 1998

(30) Foreign Application Priority Data

Jul. 15, 1996 (CH) .............................................. 1752/96

(51) Int. Cl.$^7$ .............................................. C01B 31/24

(52) U.S. Cl. ................................... 423/419.1; 423/420.2
(58) Field of Search ..................... 23/293 A; 423/419.1, 423/420.2; 106/463

(56) References Cited

U.S. PATENT DOCUMENTS 3,650,757 A * 3/1972 Irie et al. .................. 423/419.1
4,059,149 A * 11/1977 Harrison ....................... 166/64

* cited by examiner

*Primary Examiner*—Stuart L. Hendrickson
(74) *Attorney, Agent, or Firm*—Woodard, Emhardt, Naughton, Moriarty & McNett

(57) ABSTRACT

A process for the production of powders by precipitation from a liquid reaction mixture comprises passing along a tubular reactor a segmented reaction flow comprised of discrete volumes of the reaction mixture separated by discrete volumes of a separating fluid which is substantially immiscible with said reaction mixture, the residence time of said discrete volumes of reaction mixture in the reactor being sufficient for the precipitation reaction to be effected.

19 Claims, 4 Drawing Sheets

PRODUCTION OF POWDERS

This is a National Stage Application of PCT/EP97/03817, filed Jul. 15, 1997.

The present invention relates to the production of powders by a precipitation reaction.

Various industrially important powders are produced by precipitation reactions. Thus for example, copper oxalate may be produced by reaction of a solution containing copper ions with one containing oxalate ions. A further example is a mixed yttrium and barium oxalate which may be precipitated by reaction of a solution containing yttrium and barium ions with one containing oxalate ions.

Such precipitation processes are frequently conducted using batch reactors. However a problem exists with batch reactors in that it is difficult to produce a good compositional homogeneity and the problem becomes more severe as the size of the volume of the reactor is increased for the purposes of "scaling-up". As a result, the product obtained may have a wide range of particle sizes and/or non-uniform particle morphologies.

It is also known to effect such precipitation reactions in continuous flow reactors but parabolic flow profiles are generated therein resulting in similar disadvantages to those mentioned in relation to batch reactors.

It is therefore an object of the invention to obviate or mitigate the abovementioned disadvantages.

According to the present invention there is provided a process for the production of powders by precipitation from a liquid reaction mixture, the method comprising passing along a tubular reactor a segmented reaction flow comprised of discrete volumes of the reaction mixture separated by discrete volumes of a separating fluid which is substantially immiscible with said reaction mixture, the residence time of said discrete volumes of reaction mixture in the reactor being sufficient for the precipitation reaction to be effected.

In accordance with the invention, therefore, the precipitation reaction is effected by sub-dividing the reaction mixture into a plurality of discrete volumes or segments which are passed, preferably under a plug flow conditions along a tubular reactor separated by discrete volumes of a separating fluid which is immiscible with the reaction mixture. As such, a plurality of individual, and separate, volumes of the reaction mixture pass along the tubular reactor. Within each volume of the reaction mixture, the conditions for the precipitation reaction are substantially identical so that a uniform product is obtained from each volume of the reaction mixture.

In this respect, it is particularly preferred that
(i) the individual volumes of the reaction mixture are of similar (and ideally equal) size; and
(ii) the individual volumes of the separating fluid are of similar (and ideally equal) size (although not necessarily the same size as that of the reaction mixture).

This ensures that the residence time for all volumes of the reaction mixture in the tubular reactor is substantially the same to ensure uniform reaction conditions in each such batch.

It is a requirement of the separating fluid that it is substantially immiscible with the reaction mixture (at least under the conditions prevailing in the tubular reactor) to ensure that a segmented flow comprised of a plurality of discrete volumes of the reaction mixture (separated by discrete volumes of the separating fluid) may pass along the tubular reactor. It should also be ensured that the separating fluid is non-reactive towards the reaction mixture (at least under the conditions of the tubular reactor). Provided these conditions are satisfied, the separating fluid may be a gas such a air, nitrogen, oxygen, a rare gas (e.g. argon) carbon dioxide or hydrogen. Alternatively the separating fluid may be a liquid, e.g. an alkane, a petroleum derivative (e.g. kerosene), liquid paraffin, oil or silicone oil.

Depending on the particular precipitation reaction, the segmented flow may be produced either by
(i) pre-mixing the reactants and then segmenting a stream of the resultant mixture with the separating fluid or
(ii) segmenting a stream of one liquid reactant with the separating fluid thereby producing a precursor segmented reaction flow and then admixing the liquid reactant portion thereof with the remaining reactant(s) to produce the final reaction segmented flow.

The procedure (i) may, in particular, be used where the precipitation reaction is initiated by an external stimulus, e.g. heat or light. Procedure (ii) will generally be appropriate when the precipitation reaction proceeds relatively quickly after admixing of the reactants. In either case, it is highly desirable that the reactants are thoroughly admixed together.

The segmented flow may be produced from continuous streams of the liquid reaction mixture (or a liquid component thereof) and the separating fluid immiscible therewith by passing said streams along separate, respective conduits to a common segmenting reaction. The configuration of this region, and the flow rates of said streams, are set such that discrete volumes of the reaction mixture (or liquid component thereof) and the separating fluid alternately enter, and occupy the cross-section of, the segmenting region so that a segmented flow exits the outlet thereof. By way of a simple (and non-limiting) explanation as to the way in which the segmented flow may be produced, consider that the segmented fluid is a gas. In this case, it may consider that the liquid reaction mixture (or liquid component thereof) is able to pass along the segmenting region but periodically a bubble of the gas enters, and occupies the cross-section of, the segmenting region thus interrupting liquid flow therealong and thus producing the desired segmented flow. Similar considerations apply to the case where the segmenting fluid is a liquid. For any particular arrangement of segmenting region, it is a relatively simple matter to adjust the flows thereto so as to produce a segmented flow in the manner described.

The method of the invention may be applied to the production of inorganic or organic powders. The invention may be used, for example, for preparing oxalates (such as a mixed oxalate) of an alkali, alkaline earth and/or transition metal by (co-) precipitation in aqueous or alcohol medium. Alternatively the invention may be used to produce a sulfide or a mixed sulfide of at least one transition metal. Such a sulfide may be produced, for example, from a solution of the transition metal ion(s) and thioacetamide, the solution being heated to generate the precipitating anion. Further possibilities are the synthesis of oxides, mixed oxides, carbonates, mixed carbonates, hydroxides or hydroxycarbonates by precipitation or coprecipitation in aqueous or alcoholic medium in the presence of urea which is heated to generate the precipitating anion.

The invention will be further described by way of example only with reference to the accompanying drawings, in which:

FIG. 1 schematically illustrates the invention;

Figure 5:
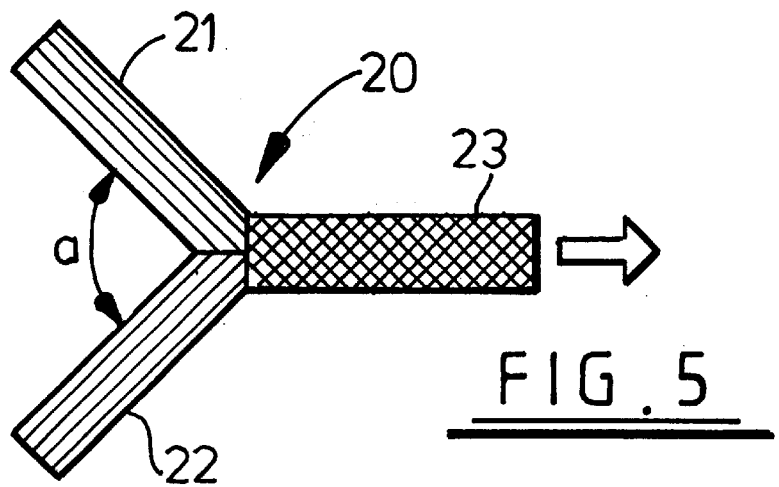
Figure 6:
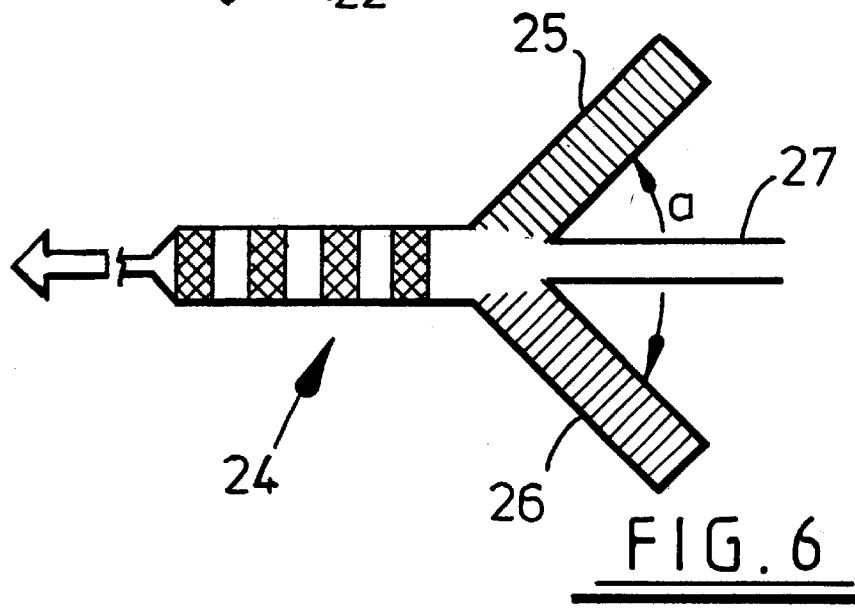

FIG. 5 schematically illustrates an arrangement for mixing two liquid reactants;

FIG. 6 illustrates an apparatus for producing a segmented flow; and

Figure 7:
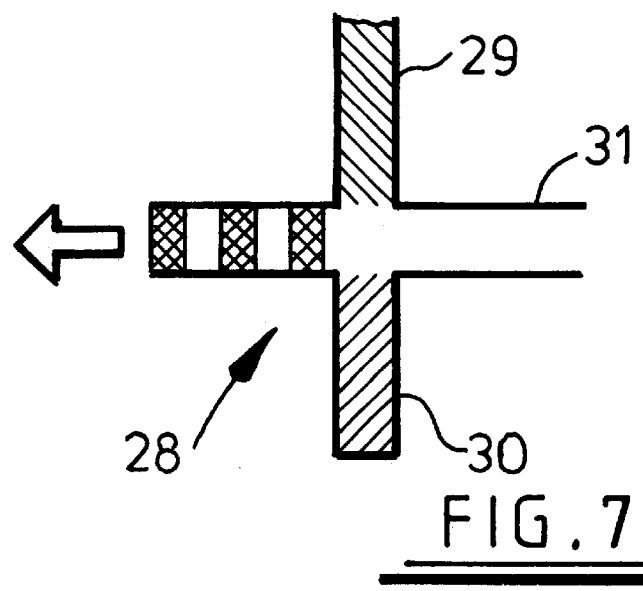

FIG. 7 illustrates a further apparatus for producing a segmented flow.

Figure 1:
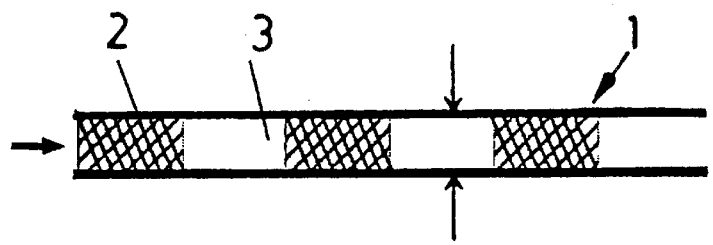

Referring firstly to FIG. 1, the process illustrated therein employs a tubular reactor 1 along which are alternately supplied (from left to right as viewed in FIG. 1) individual volumes or segments 2 of a reaction mixture (which yields a desired powder product) and segments 3 of a "separating" fluid (gas or liquid) which is substantially immiscible with the reaction mixture. As such, segments 2 and 3 pass alternately and individually along the reactor and the powder is produced in the segments 2 during the residence time thereof in the reactor. Typically the residence times of segments 2 and 3 in the tubular reactor will be in the range of seconds to hours depending on the particular precipitation reaction under consideration.

The reactor 1 may have an inner diameter of, for example, 0.1 to 10 mm (e.g. 2 to 5 mm) and a length of a few tens of centimeters to several tens of meters, these parameters being determined according to the desired flow rate and residence time ($T_{res}$) which is given by the equation $$T_m = \frac{L_r \times S_1}{V_r + V_s}$$

where $L_t$ is the length of the tubular reactor. $S_t$ is the internal surface area of tube thereof, and $V_r$ and $V_s$ are respectively the flow rates of the reactant mixture and separating fluid.

Each segment 2 of the reactant mixture is of similar volume. Typically each such segment has a length of 2–3 times the internal diameter of the tubular reactor 1. Similarly each segment 3 of separating fluid is of similar volume to each other such segment although may be of a different volume to the segments 2. Typically segments 3 will have a length of 2–3 times the internal diameter of the tubular reactor.

Within reactor 1, all of the segments move under plug flow. As a result of this plug flow, back-mixing of successive volumes or segments 2 of the reaction mixture is prevented.

The reactor as described, and more particularly the use of segmented flow conditions employed therein, has a number of advantages.

Firstly, the segmentation of the reaction mixture favours a high uniformity of the precipitation conditions. This is contrast to batch reactions where it is difficult to keep good compositional homogeneity, the problem becoming more severe as the volume of the reactor is scaled-up.

Secondly, the flow conditions established in the reactor ensure that the reactor performs as a true plug flow reactor in that each segment 2 of reaction mixture has exactly the same residence time in the reactor. Hence, each segment 2 experiences exactly the same history and, as a result, powders obtained from each segment 2 possess very homogenous characteristics in term of chemical composition, morphology and size. Thus, precipitates with a narrow particle size distributions can be obtained.

Thirdly, the process may be readily scaled-up by using a plurality of the tubular reactors in parallel.

Overall, the illustrated process ensures a better chemical selectivity (i.e. ability to produce a product of a particular composition) due to the use of the individual segments 2 of the reactant mixture and to the suppression of parabolic flow profiles generally found in continuous tubular reactors. The reaction conditions in the segments 2 are uniform in space and time so that more exact processing conditions and constant results are usually obtained. For precipitation reactions, this promotes the formation of powders with a narrow range of chemical compositions, improved uniformity of particle morphologies and narrower particle size distributions.

An important feature of the process illustrated in FIG. 1 is the formation of the flow stream comprised of alternate segments 2 of reaction mixture and segments 3 of the separating fluid. Such a flow stream may be produced, for example, using the apparatus illustrated in FIGS. 2–4.

Figure 2:
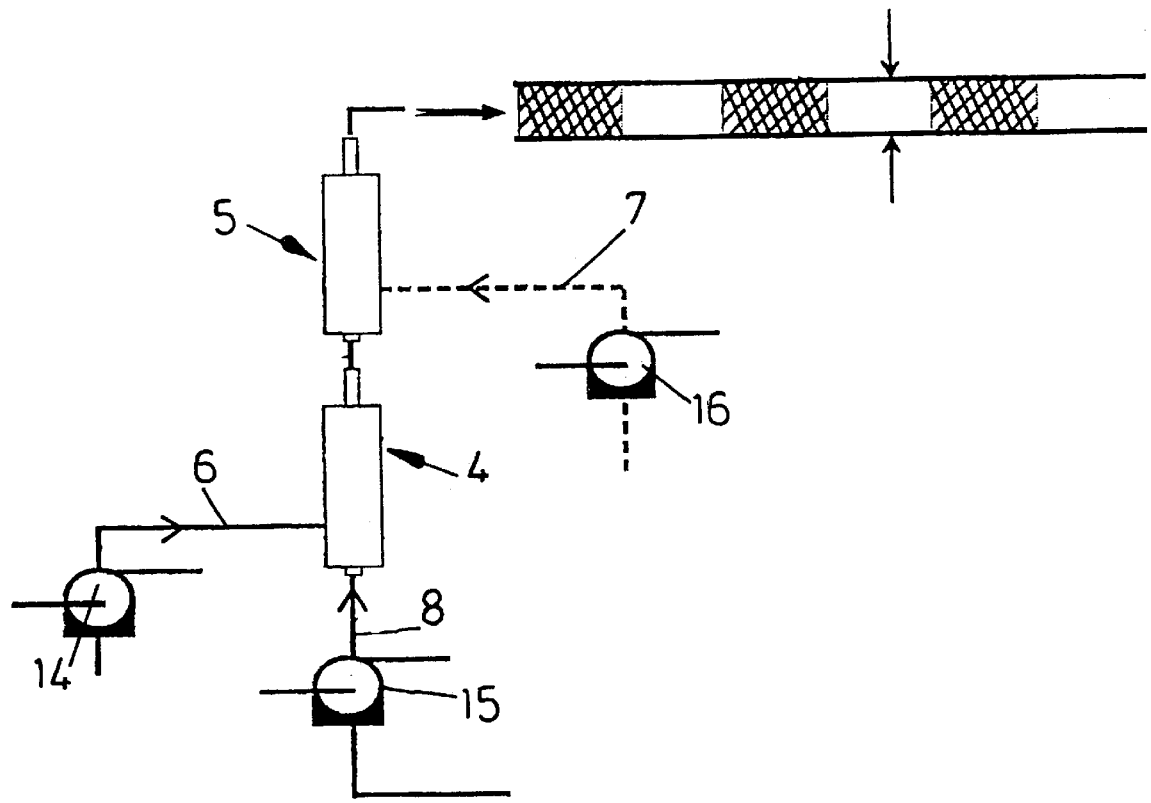
FIG. 2 illustrates one embodiment of apparatus for carrying out the method of the invention.

The apparatus of FIG. 2 comprises a tubular reactor 1 (as described above), a "segmenter" 4 positioned upstream of reactor 1, and a mixer 5 located between the segmenter 4 and reactor 1.

In the arrangement of FIG. 2, the segments 2 are formed as an admixture of (different) reactants supplied as streams 6 and 7, and the segments 3 are produced from a stream 8 of separating fluid. To understand the manner in which the segmented flow (comprised of segments 2 and 3) is produced, reference is firstly made to FIG. 3 illustrating the construction of segmenter 4.

Figure 3:
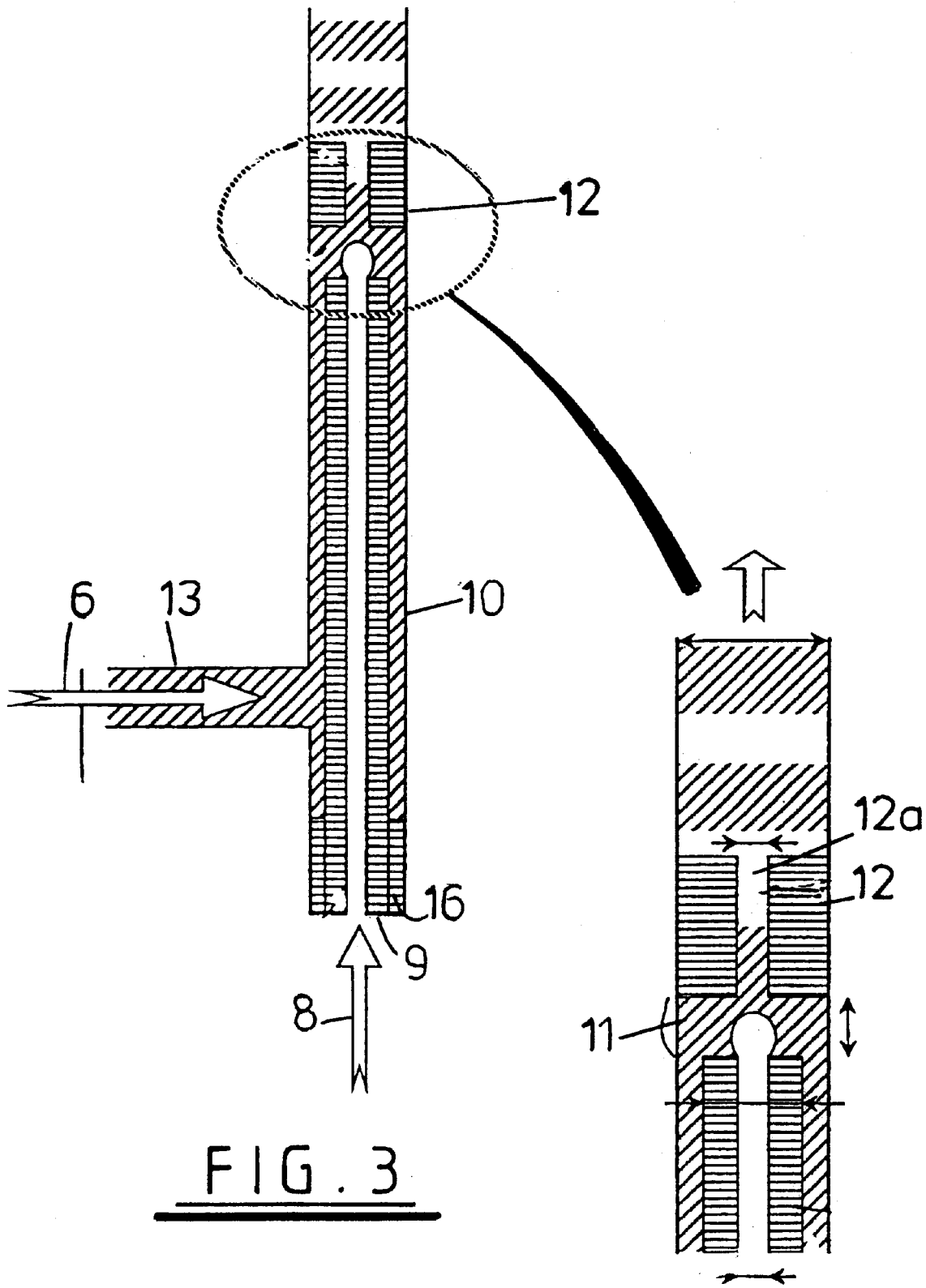
FIG. 3 is a detail of the "segmenter" illustrated in FIG. 2.

As shown in FIG. 3, the segmenter 4 comprises a first tube 9 concentrically located within a second tube 10 so that an annular space is defined between the two tubes. The inner tube 9 is of a shorter length than tube 10 and as shown in FIG. 3 a mixing chamber 11 (e.g. having a diameter of 2 mm to 10 mm) is defined in tube 10 between the downstream end of tube 9 (the upper end as viewed in FIG. 3) and a segmenting region in the form of a restrictor element 12 which is located within tube 10 and which has a central restriction 12a coaxial with the bore of tube 9.

The inner diameter of the tube 9 may, for example, be in the range 0.1 to 2 mm depending on the desired flow rate and it is possible for tube 9 in the segmenter 4 to be interchangeable with one of a different diameter. Typically the distance between the downstream end of the tube 9 and the upstream end of the restriction element 12 is in the range 0.5 to 5 mm. This distance may be made adjustable, e.g. by virtue of tube 9 being located in position by a screw thread arrangement (not shown).

The outer tube 10 (which may, for example, have an inner diameter of 2 to 5 times that of the inner tube 9) is provided with an arm 13 into which the reactant stream 6 is supplied by means of a volumetric pump 14 (see FIG. 2) which may for example be of the piston or peristaltic type. As such, the reactant stream 6 may enter, and fill, the annular space between tubes 9 and 10. The stream of separating fluid 8 is supplied by means of a volumetric pump 15 (see FIG. 2) to the upstream end of the inner tube 9. A blanking arrangement 16 provided around the upstream end of tube 9 ensures that the stream of separating fluid 8 must pass fully along the tube 9 before it encounters the reactant stream 6.

The purpose of the segmenter 4 is to produce a flow comprised of alternate segments of the reactant stream 6 and the separating fluid 8. This is achieved by setting the flow rates of the streams 6 and 8 so that periodically a discrete volume of the separating fluid 8 enters a restriction 12a (and occupies the cross-section thereof) thus, in effect, interrupting what would otherwise be a continuous flow of stream 6 therealong.

Figure 4:
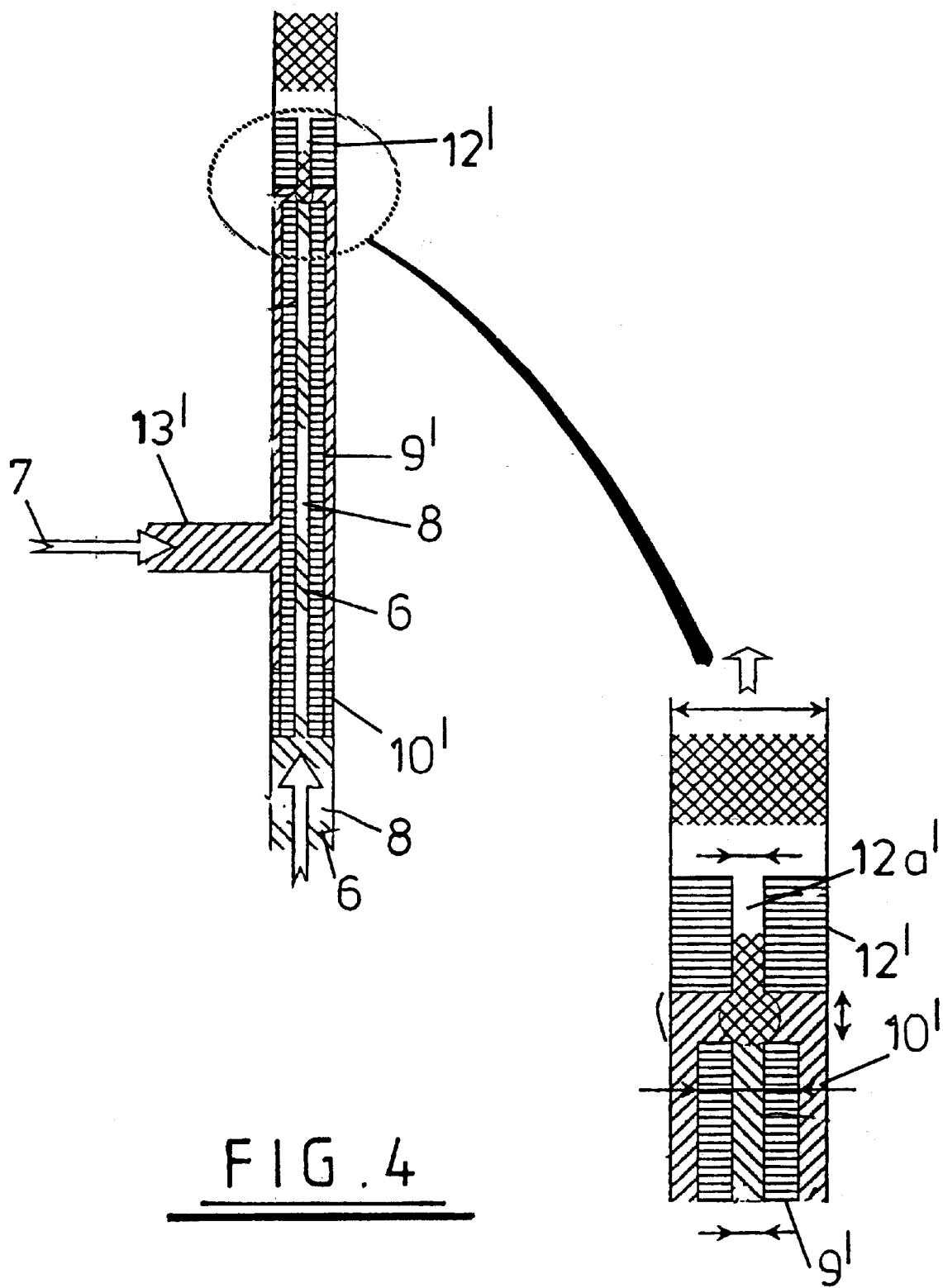
FIG. 4 is a detail of the "mixer" illustrated in FIG. 2.

This segmented flow is then passed to the mixer 5, the construction of which is illustrated in FIG. 4 of the drawings.

As will be seen in FIG. 4, the construction of mixer 5 is very similar to that of the segmenter 4 and for convenience like parts in these two items are represented by the same reference numerals but, in the case of mixer 5, additionally denoted by "'".

As will be understood from FIG. 4, the segmented flow comprised of alternate, discrete volumes of reactant 6 and separating fluid 8 is passed into the upstream end of the central tube 9' of mixer 5. The segmented flow is maintained along the length of tube 9'.

The reactant stream 7 is passed, by means of a volumetric pump 16 into the annular space between the tubes 9' and 10'. Within mixing chamber 11', the reactant stream 7 is able to mix with the reactant 6, and segments of the resulting mixture (corresponding to segments 2 in FIG. 1) are able to pass along the restriction element 12'a alternatively with segments of the immiscible separating fluid 8. This is achieved by setting appropriate flow rates for the flow of reactant 7 and that of the segmented flow of reactant 6 and separating fluid 8.

Within restriction 12' the reactants 6 and 7 are efficiently and thoroughly mixed. This is achieved by virtue of the reactants being forced together within the restriction in which average distance between flow trajectories becomes smaller, and flow may become turbulent, so that fast mass transfer is favoured.

The resultant segmented flow of reaction mixture 2 and separating fluid 8 is then passed to tubular reactor 1 (see FIG. 1 and description relating thereto).

The arrangement described with reference to FIGS. 2 to 4 is particularly suitable for reactions in which a precipitate (i.e. the desired powder) is formed relatively rapidly upon mixing of reactants 6 and 7 since, in the arrangement of FIGS. 2 to 4, such mixing only takes place immediately before the tubular reactor 1.

The invention does however also extend to precipitation reactions in which the reactants may be mixed together under predetermined conditions (e.g. ambient conditions) such that precipitation is only effected by application of an external stimulus, e.g. light or an increase in temperature. In this case, the apparatus 4 (previously referred to as the segmenter) may be used as a mixer to effect mixing of the two liquid reactant streams, one being passed along the inner tube 9 and the other through arm 13, thorough mixing being effected within the restriction 12'a. The mixed reactant stream may then pass through the arm 13' of apparatus 5 whilst a separating fluid passes along the inside of tube 9'. Therefore, in this case, apparatus 4 acts as a mixer and apparatus 5 acts as a segmenter. It will however be appreciated that, in this case, the apparatus 4 may be replaced by any other suitable mixing arrangement. Precipitation may subsequently be initiated by applying the stimulus (e.g. light or heat) segmented flow in reactor 1.

It will be appreciated that the tubular reactor 1, segmenter 4 and mixer 5 may be of any material which is not degraded and which remains unaltered in contact with the reactants and separating fluid. Further criteria for the choice of material are its ability to be wetted by the reactants and separating fluid and non-adherence to the precipitated particles. Examples of suitable materials include plastics (e.g. PMMA, PTFE, PE, PO, and the like), glasses (e.g. chemistry glass, bovosilicate glass, vitreous silica and the like) and metals (e.g. stainless steel, aluminium, titanium or alloys thereof, and the like.

FIG. 5 illustrates an apparatus 20 which may be used for producing a mixture of liquid reactants prior to segmentation of the mixture. The mixer apparatus 20 is a Y-shaped mixer having converging arms 21 and 22 along which reactants may be supplied and a stem 32 along which the mixture exits the apparatus. The angle α between the arms 21 and 22 may be varied.

The apparatus 24 illustrated in FIG. 6 is for mixing liquid reactant streams and providing a segmented flow. More particularly, the apparatus 24 comprises angled arms 25 and 26 along which respective reactant streams are supplied and a conduit 27 (disposed between the arms 25 and 26) along which separating fluid is supplied. The reactant streams mix on exit from the arms 25 and 26 and a segmented flow of the mixture is produced by use of an appropriate flow rate for the segmenting fluid in conduit 27.

The apparatus 28 illustrated in FIG. 7 is somewhat similar to that of FIG. 6 save that the arms 29 and 30 along which reactant streams are supplied are directly opposed to each other, separating fluid being supplied along arm 31.

The invention will be further described with reference to the following non-limiting Examples

EXAMPLE 1

Using apparatus as illustrated in FIGS. 2 to 4, a reaction mixture comprised of an admixture of equal volumes of a solution of $Cu^{2+}$ ions ($2+10^{-3}$ mol $l^{-1}$) and a solution comprised of oxalate ions ($2 \times 10^{-3}$ mol $l^{-1}$) was passed as discrete segments (volume=0.1–2 cm$^3$) separated by air bubbles of similar volume along a tubular reactor having a length of 5 m and internal diameter of 3 mm. The residence time of the segments in the reactor was 15 minutes and the reaction was conducted at a temperature of less than 50° C.

The product obtained was compared with that produced in a batch reactor using same concentrations, temperatures and reaction time.

It was found that the copper oxalate produced by the method of the invention had a narrower size distribution, a larger mean particle size, a smaller crystallate size and a more regular morphology (sticks) than the product of the batch reactor. This indicated that the aggregation kinetics were faster in the tubular reactor whereas the crystallites grew faster, and were consequently larger, in the batch reactor.

EXAMPLE 2

An apparatus of the type illustrated in FIGS. 2–4 was used to produce a segmented reaction flow from equal volumes of separate streams of (i) a solution comprised of $Y^{34}$ ions ($1.3 \times 10^{-3}$ mol $l^{31\ 1}$) and $Ba^{2+}$ ions ($1.3 \times 10^{-3}$ mol $l^{-1}$).

(ii) a solution comprised of oxalate ions ($4.7 \times 10^{-3}$ mol $l^{-1}$), and (iii) air The segmented reaction flow was passed along a tubular reactor having a length of 5 m and an internal diameter of 3 mm in which each segment of the reaction mixture (volume=0.1 to 2 cm$^3$) had a residence time of 15 minutes. The reaction was conducted at a temperature of less than 50° C.

The product was the reaction comprised particles having a single octahedral morphology and a well defined chemical composition ($Y_2Ba_4(C_2O_4)_7 \cdot xH_2O$).

Under batch conditions employing the same concentrations, temperature and reaction time, the product comprised a mixture of $Y_2Ba_4(C_2O_4)_7 \cdot xH_2O$ (octahedral particles) and $Y_2Ba_2(C_2O_4)_5 \cdot yH_2O$ (pinacoidal particles).

This Example thus illustrates use of the segmented flow procedure to improve chemical selectivity of the precipitated product.

EXAMPLE 3

A solution comprised of $Y^{3+}$ cations ($2.5 \times 10^{-3}$ mol $l^{-1}$) was admixed with an equal volume of one comprised of urea ($75 \times 10^{-2}$ mol $l^{-1}$) and the resultant mixture was passed as a segmented flow in which discrete volumes (0.1–1 cm$^3$) of reaction mixture separated by air bubbles were passed along a tubular reactor having a length of 7.5 m and an internal diameter of 3 mm so as to have a residence time of 120 min. The temperature along the reactor was >50° C. so to decompose the urea to generate $CO_3^{2-}$ and $OH^+$ as precipitating anions.

The product of the reaction comprised spherical particles of yttrium hydroxycarbonate, $Y(OH)CO_3$, having a larger particles size and narrower size distribution than obtained used a batch reaction employing similar conditions. Similar results were obtained using kerosene as the segmenting fluid.

The procedure using the tubular reactor was repeated but using a continuous flow of reaction mixture without segmentation thereof. This resulted in a velocity gradient being established in the reactor so that the particles evolved with various residence times leading to a very heterogeneous size distribution.

EXAMPLE 4

A solution comprised of $Zn^{2+}$ cations ($5 \times 10^{-2}$ mol l$^{-1}$) was admixed with an equal volume of a solution of thioacetamide ($4 \times 10^{-1}$ mol l$^{-1}$) and the mixture passed as a segmented flow in which discrete volumes (0.1–1 cm$^3$) of reaction mixture separated by air bubbles were passed along a tubular reactor having a length of 7.5 m and an internal diameter of 3 mm so as to have a residence time of 30 minutes. The temperature along the reactor was >50° C. so as to decompose the tioacetamide to produce $S^{2-}$ as a precipitating anion thus yielding ZnS as the product of the reactions.

A similar reaction was conducted using a batch reactor.

It was found that the tubular reactor and the batch reactor could be used to synthesise both nanoparticles (30 nm in size) and sub-micrometer particles (700–1500 nm in size) of ZnS with narrow size distribution. In the tubular reaction, a larger mean particle size was obtained for the sub-micrometer ZnS particles. The particle size range was the same in the batch and tubular reactors for ZnS nanoparticles but the latter had the advantage of continuous operations.

What is claimed is:

1. A process for the production of a powder by precipitation from a liquid reaction mixture, the method comprising passing along a tubular reactor a segmented reaction flow comprised of discrete volumes of the reaction mixture separated by discrete volumes of a separating fluid which is substantially immiscible with said reaction mixture, the residence time of said discrete volumes of reaction mixture in the reactor being sufficient for the precipitation reaction to be effected, wherein the powder is selected from the group consisting of a carbonate, mixed carbonate, or hydroxycarbonate, wherein the reaction segmented flow is produced by passing the reaction mixture or a component thereof and the separating fluid to a chamber having a restricted outlet from which the segmented flow issues, and further wherein the passing comprises passing the reaction mixture or a component thereof and the separating fluid through a segmentation arrangement comprised of two concentric tubes, said chamber being provided at the outlet of the inner of the tubes.

2. A process as claimed in claim 1 wherein the innermost tube has an internal diameter of 0.1 to 2 mm.

3. A process as claimed in claim 1 wherein the distance between the outlet of the innermost tube and the inlet of the restriction is in the range 0.1 to 5 mm.

4. A process as claimed in claim 1 wherein said chamber has an internal diameter of 2 mm to 10 mm.

5. A process as claimed in claim 1 wherein the separating fluid is passed to said chamber along the innermost tube.

6. A process as claimed in claim 1 wherein the precipitation reaction is initiated by application of an external stimulus to the reaction mixture.

7. A process as claimed in claim 6 wherein the external stimulus is heat or light.

8. A process as claimed in claim 1 wherein the segmented reaction flow is prepared by separately passing a first component of the reaction mixture and the separating fluid into said chamber thereby producing a precursor segmented reaction flow comprised of discrete volumes of said component of the reaction mixture separated by discrete volumes of the separating fluid, and the segmented reaction flow is produced by admixing said discrete volumes of the reaction component with the remaining component(s) of the reaction mixture.

9. A process as claimed in claim 8 wherein the segmented reaction flow is prepared from said precursor flow by injecting said latter flow and the further component(s) of the reaction mixture to a chamber having a restricted outlet under conditions such that said further component(s) of the reaction mixture become admixed with the discrete volumes of said first component of the reaction mixture whereby the segmented reaction flow is produced.

10. A process for the production of a powder by precipitation from a liquid reaction mixture, the method comprising passing along a tubular reactor having an internal diameter of 0.1 to 10 mm a segmented reaction flow comprised of discrete volumes of the reaction mixture separated by discrete volumes of a separating fluid which is substantially immiscible with said reaction mixture, the residence time of said discrete volumes of reaction mixture in the reactor being sufficient for the precipitation reaction to be effected, wherein the powder is selected from the group consisting of a carbonate, mixed carbonate, or hydroxycarbonate, wherein the segmented reaction flow is produced in a mixing arrangement comprised of two concentric tubes, said chamber being provided at the outlet of the inner of the two tubes, the segmented reaction flow being prepared by separately passing a first component of the reaction mixture and the separating fluid into said chamber thereby producing a precursor segmented reaction flow comprised of discrete volumes of said component of the reaction mixture separated by discrete volumes of the separating fluid, the segmented reaction flow being produced by admixing said discrete volumes of the reaction component with the remaining component(s) of the reaction mixture, the segmented reaction flow further being prepared from said precursor flow by injecting said latter flow and the further component(s) of the reaction mixture to a chamber having a restricted outlet under conditions such that said further component(s) of the reaction mixture become admixed with the discrete volumes of said first component of the reaction mixture whereby the segmented reaction flow is produced.

11. A process as claimed in claim 10 wherein the innermost tube of the mixing arrangement has an internal diameter of 0.1 to 2 mm.

12. A process as claimed in claim 10 wherein the distance between the outlet of the innermost tube of the mixing arrangement and the inlet of the restriction is in the range 0.1 to 5 mm.

13. A process as claimed in claim 10 wherein the chamber of the mixing arrangement has a diameter of 2 mm to 10 mm.

14. A process as claimed in claim 10 wherein the precursor segmented reaction flow is passed to the chamber of the mixing arrangement along the innermost tube thereof.

15. A process for the production of a powder by precipitation from a liquid reaction mixture, the method comprising passing along a tubular reactor a segmented reaction flow comprised of discrete volumes of the reaction mixture separated by discrete volumes of a separating fluid which is substantially immiscible with said reaction mixture, the residence time of said discrete volumes of reaction mixture in the reactor being sufficient for the precipitation reaction to be effected, wherein the powder is selected from the group consisting of a carbonate, mixed carbonate, or hydroxycarbonate, wherein the separating fluid is a gas.

16. A process as claimed in claim 15 wherein the separating fluid is air, nitrogen, oxygen, a rare gas, carbon dioxide or hydrogen.

17. A process as claimed in claim 1 wherein the separating fluid is a liquid.

18. A process as claimed in claim 17 wherein the reaction mixture is aqueous and the separating liquid is selected from the group consisting of an alkane, a petroleum derivative, liquid paraffin, oil, and silicone oil.

19. A process as claimed in claim 18 wherein the separating liquid is kerosene.

* * * * *